(12) United States Patent
Tsai

(10) Patent No.: US 6,625,819 B1
(45) Date of Patent: Sep. 30, 2003

(54) HEADPHONE TYPE EARPIECE ASSEMBLY AND EARPIECES FOR THE HEADPHONE TYPE EARPIECE ASSEMBLY

(76) Inventor: Kai-Mou Tsai, 13/F, No. 418, Chung Yang N. Rd., Sec. 2, Peitou District, Taipei City (TW)

( * ) Notice: Subject to any disclaimer, the term of this patent is extended or adjusted under 35 U.S.C. 154(b) by 0 days.

(21) Appl. No.: 10/331,472

(22) Filed: Dec. 31, 2002

(51) Int. Cl.[7] .................................................. A42B 1/06
(52) U.S. Cl. ............................................ 2/209; 181/129
(58) Field of Search ............................... 2/209, 423, 174; 128/866; 181/129, 128, 136; 381/383, 379, 378, 374, 370, 330

(56) References Cited

U.S. PATENT DOCUMENTS

| | | | | |
|---|---|---|---|---|
| 2,439,289 A | * | 4/1948 | Fanslow | 2/209 |
| 2,597,508 A | * | 5/1952 | Majewski | 2/209 |
| 3,354,471 A | * | 11/1967 | Longo | 2/174 |
| 4,713,843 A | * | 12/1987 | Duncan | 2/209 |
| 4,850,055 A | * | 7/1989 | Hwang | 2/209 |
| 4,971,072 A | * | 11/1990 | Randall | 2/174 |
| 5,790,683 A | * | 8/1998 | Salzani | 381/370 |
| 6,580,800 B1 | * | 6/2003 | Yamasaki et al. | 381/379 |
| 2003/0085069 A1 | * | 5/2003 | Tsai | 181/129 |

FOREIGN PATENT DOCUMENTS

| | | | | |
|---|---|---|---|---|
| DE | 148274 | * | 2/1904 | 2/209 |
| FR | 2536253 A | * | 5/1984 | 2/209 |

* cited by examiner

*Primary Examiner*—Rodney M. Lindsey
(74) *Attorney, Agent, or Firm*—Rosenberg, Klein & Lee

(57) ABSTRACT

A headphone type earpiece assembly having two earpieces adapted for protecting the user's ears and keeping the user's ear warm and a cord member connected between the earpieces is disclosed. Each earpiece has a soft cloth covering supported with a flat frame, and a clamping plate pivoted to the flat frame and disposed outside the soft cloth covering for securing the respective earpiece to one of the user's ears. The clamping plate has a horizontal front hook for hanging on the top side of the ear, and a vertical clamping portion for clamping on the tragic lamina of the ear.

6 Claims, 6 Drawing Sheets

HEADPHONE TYPE EARPIECE ASSEMBLY AND EARPIECES FOR THE HEADPHONE TYPE EARPIECE ASSEMBLY

BACKGROUND OF THE INVENTION

The present invention relates to a headphone type earpiece assembly, and more particularly, to such a headphone type earpiece assembly, which is comfortable in use and, does not slip when fastened to the head.

FIGS. 9 and 10 show a headphone type earpiece assembly according to the prior art. This structure of headphone type earpiece assembly comprises two earpieces 4, and a smoothly arched headband 5 of resilient material. The smoothly arched headband 5 imparts an inward pressure to the earpieces 4, causing the earpieces 4 to be secured to the user's ears. This structure of headphone type earpiece assembly is still not satisfactory in function because of the following drawbacks.

1. The high inward pressure from the arched headband 5 causes the user to feel uncomfortable.
2. When fastened to the user's head, a gap 6 may be left between the arched headband 5 and the user's head, and the headphone type earpiece assembly tends to slip from position or to disturb the shape of the user's hair 32.
3. The size of the arched headband 5 cannot be adjusted to fit different users. If not in perfect fit, the earpieces 4 cannot be kept in close contact with the user's ears.
4. Because the arched headband 5 is not collapsible, the headphone type earpiece assembly occupies much storage space when not in use.

SUMMARY OF THE INVENTION

The present invention has been accomplished to provide a headphone type earpiece assembly, which eliminates the aforesaid drawbacks. It is one object of the present invention to provide a headphone type earpiece assembly, which can positively be fastened to the user's ears to well protect the user's ears and to keep the user's ears warm. It is another object of the present invention to provide a headphone type earpiece assembly, which is comfortable in use and gives no pressure to the user's cheeks when installed. It is still another object of the present invention to provide a headphone type earpiece assembly, which occupies less storage space when received. To achieve these and other objects of the present invention, the headphone type earpiece assembly comprises two earpieces adapted for protecting the user's ears and keeping the user's ear warm, and a cord member connected between the earpieces. Each earpiece comprises a soft cloth covering supported with a flat frame, and a clamping plate pivoted to the flat frame and disposed outside the soft cloth covering for securing the respective earpiece to one of the user's ears. The clamping plate has a horizontal front hook for hanging on the top side of the ear, and a vertical clamping portion for clamping on the tragic lamina of the ear. According to an alternate form of the present invention, the clamping plate is comprised of a rear half forming the rear finger strip and the respective lugs, and a front half forming the horizontal front hook and the vertical front clamping portion and detachably connected to the rear half. The rear half has a receptacle and a retaining hole in the receptacle. The front half has a plug rod insertable in the receptacle, and a retaining portion protruded from the plug rod for engaging the retaining hole in the receptacle.

DETAILED DESCRIPTION OF THE PREFERRED EMBODIMENT

Figure 1:
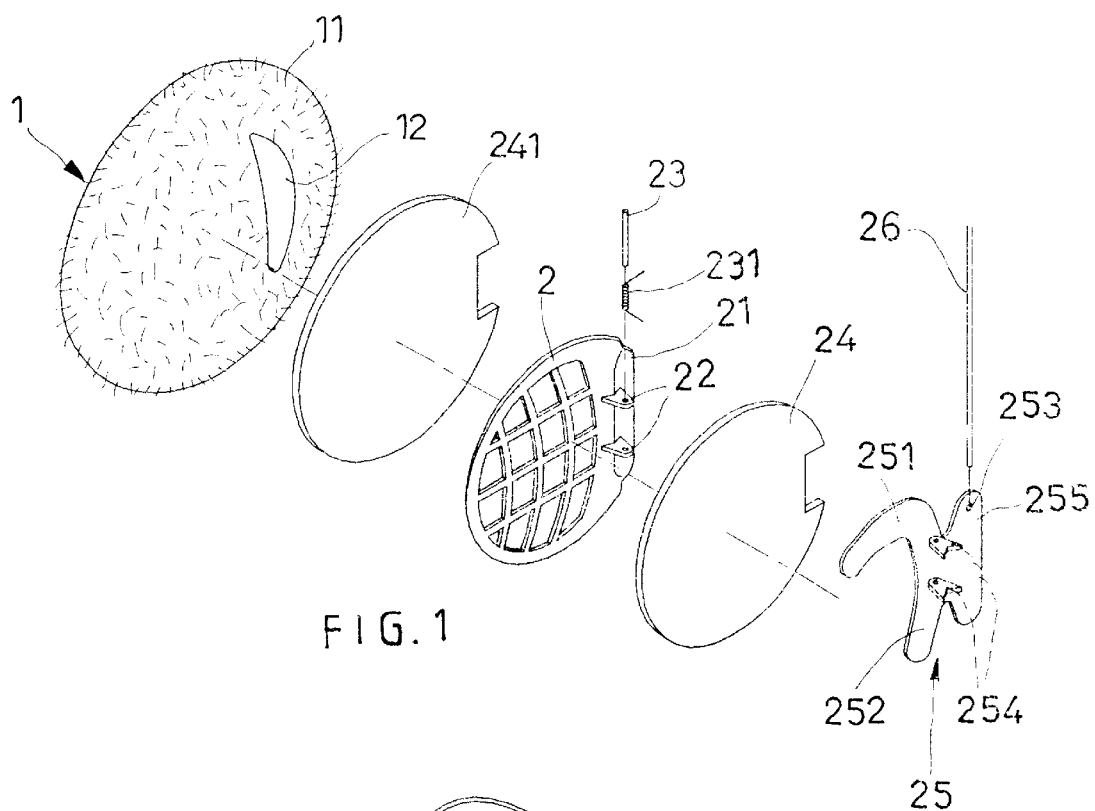
FIG. 1 is an exploded view of an earpiece according to the present invention.
Figure 2:
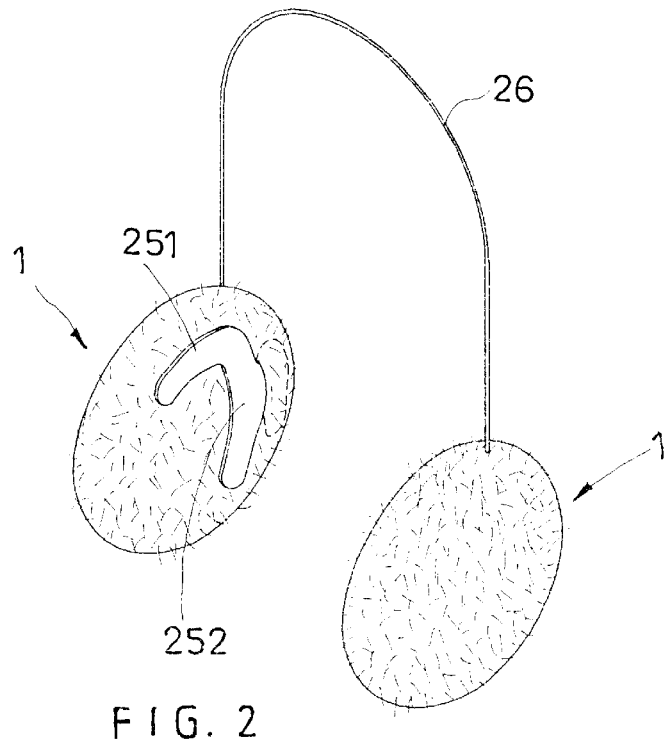
FIG. 2 is an elevational view of a headphone type earpiece assembly according to the present invention.
Figure 3:
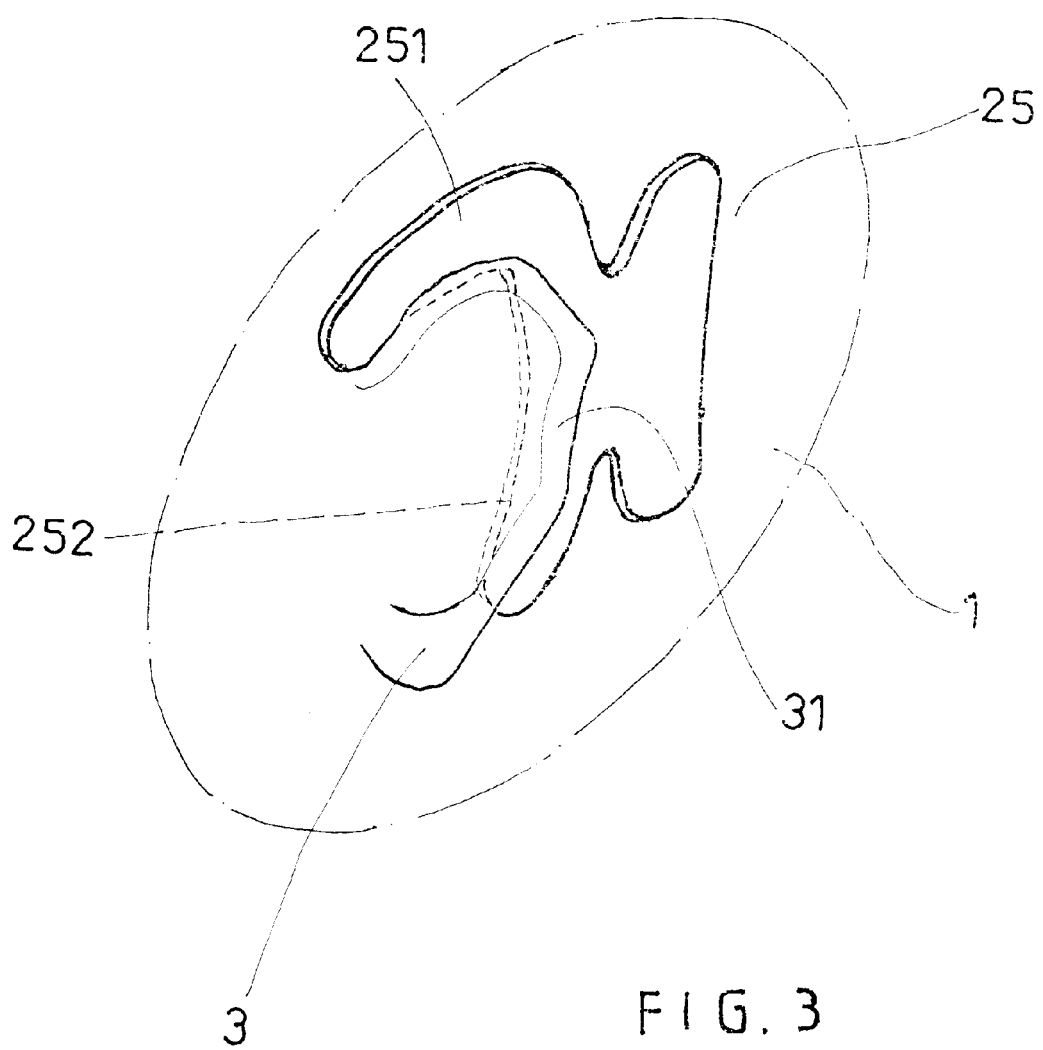
FIG. 3 is a schematic drawing showing the horizontal front hook of the clamping plate hung on the top of the ear, the vertical front clamping portion of the clamping plate clamped on the tragic lamina of the ear according to the present invention.
Figure 4:
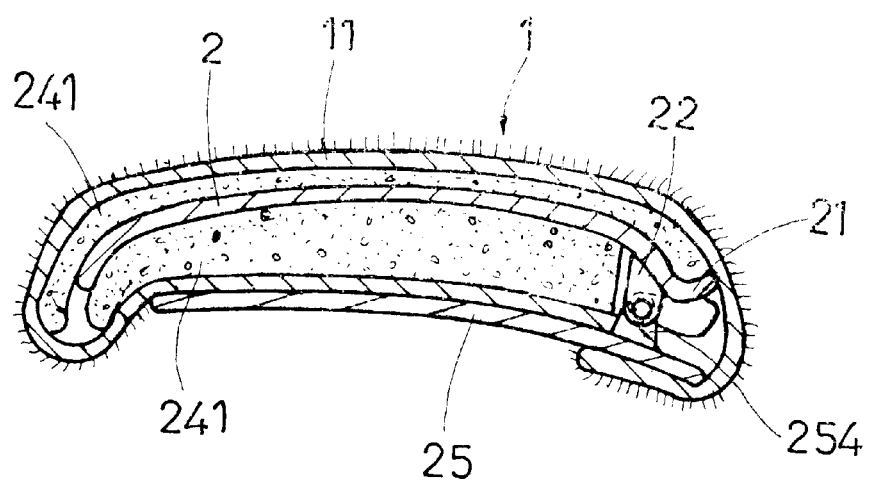
FIG. 4 is a sectional view of an earpiece according to the present invention.

Referring to FIGS. from 1 through 4, a headphone type earpiece assembly in accordance with the present invention is shown comprised of two earpieces 1, and a cord member 26 connected between the earpieces 1. Each earpiece 1 comprises a soft cloth covering 11, a flat frame 2, two soft pads 24 and 241, and a clamping plate 25. The soft cloth covering 11 has a back hole 12. The flat frame 2 is inserted through the back hole 12 into the inside of the soft cloth covering 11 to support the soft cloth covering 11 in shape. The soft pads 24 and 241 are respectively supported on the front and back sides of the flat frame 2 inside the soft cloth covering 11. The flat frame 2 is slotted for ventilation, having a side flange 21 and two lugs 22 protruded from the back side of the side flange 21. The clamping plate 25 comprises a horizontal front hook 251, a vertical front clamping portion 252, a rear finger strip 255, and two parallel lugs 254 on the middle. The lugs 254 are pivotally fastened to the lugs 22 of the flat frame 2 by a pivot pin 23. A torsional spring 231 is mounted on the pivot pin 23 and connected between the flat frame 2 and the rear finger strip 255 of the clamping plate 25 to hold the clamping plate 25 in the close position. The clamping plate 25 further has a wire hole 253 in the rear finger strip 255 for the connection of one end of the cord member 26. After installation of the clamping plate 25 in the flat frame 2, the horizontal front hook 251 and the vertical front clamping portion 252 are disposed outside the soft cloth covering 1 and forced by the spring force of the torsional spring 231 to press the soft cloth covering 11 against the soft pad 24 and the flat frame 2.

Figure 5:
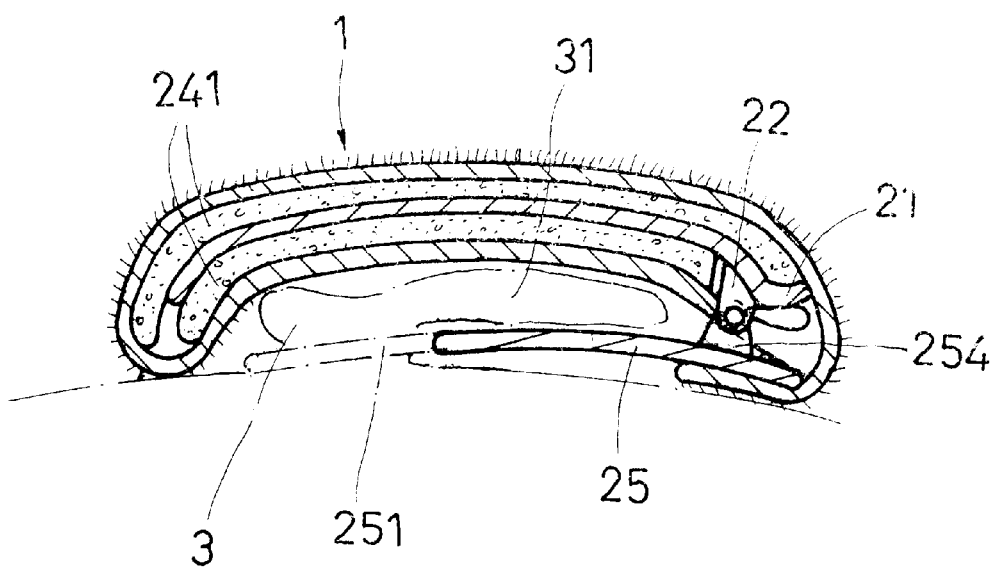
FIG. 5 is similar to FIG. 4 but showing the earpiece fastened to the ear.
Figure 6:
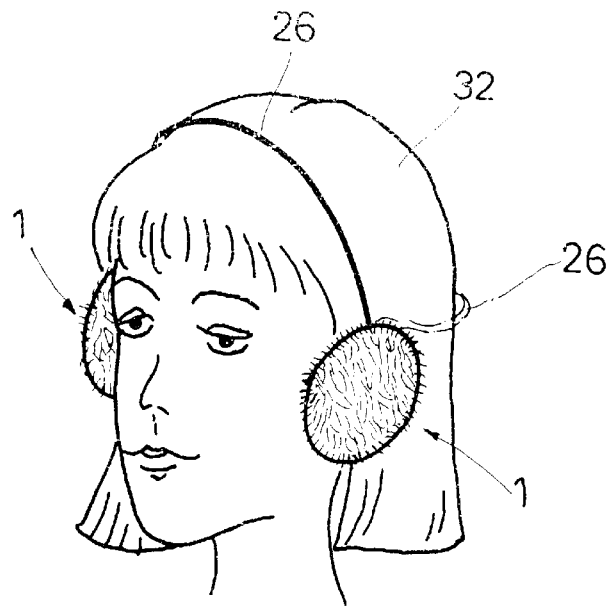
FIG. 6 is an applied view of the present invention, showing the headphone type earpiece assembly fastened to the user's head and covered on the user's ears.

Referring to FIGS. 5 and 6 and FIGS. 3 and 4 again, when squeezing the side flange 21 of the flat frame 2 and the rear finger strip 255 of the clamping plate 25 with the fingers, the clamping plate 25 of the respective earpiece 1 is forced to turn about the corresponding pivot pin 23 from the close position to an open position, enabling the respective earpiece 1 to be fastened to the corresponding ear 3. When installed, the horizontal front hook 251 of the clamping plate 25 is hung on the top side of the ear 3, and the vertical front clamping portion 252 of the clamping plate 25 is clamped on the tragic lamina 31 of the ear 3. Further, the cord member 26 can be adjusted to hold down the user's hair 32.

Figure 7:
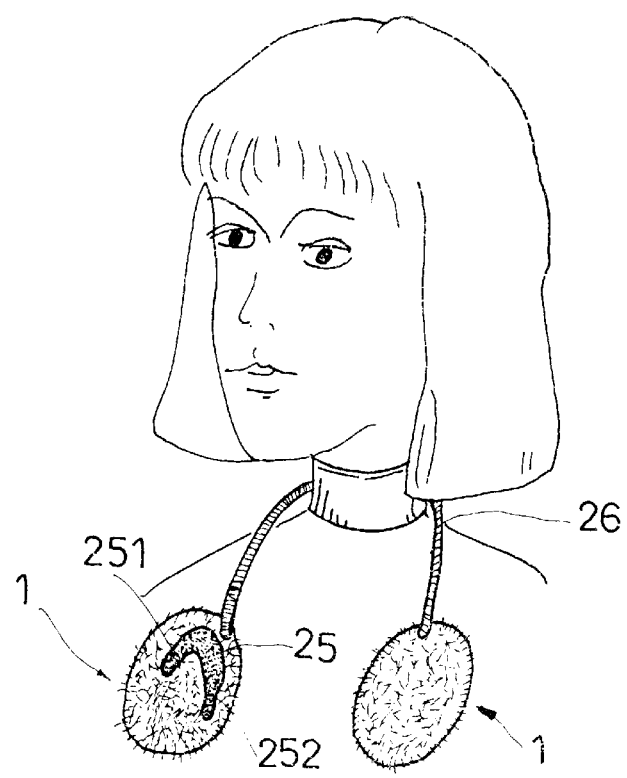
FIG. 7 illustrates the headphone type earpiece assembly hung on the user's neck according to the present invention.

Referring to FIG. 7, when not in use, the headphone type earpiece assembly can be hung on the user's neck.

Figure 8:
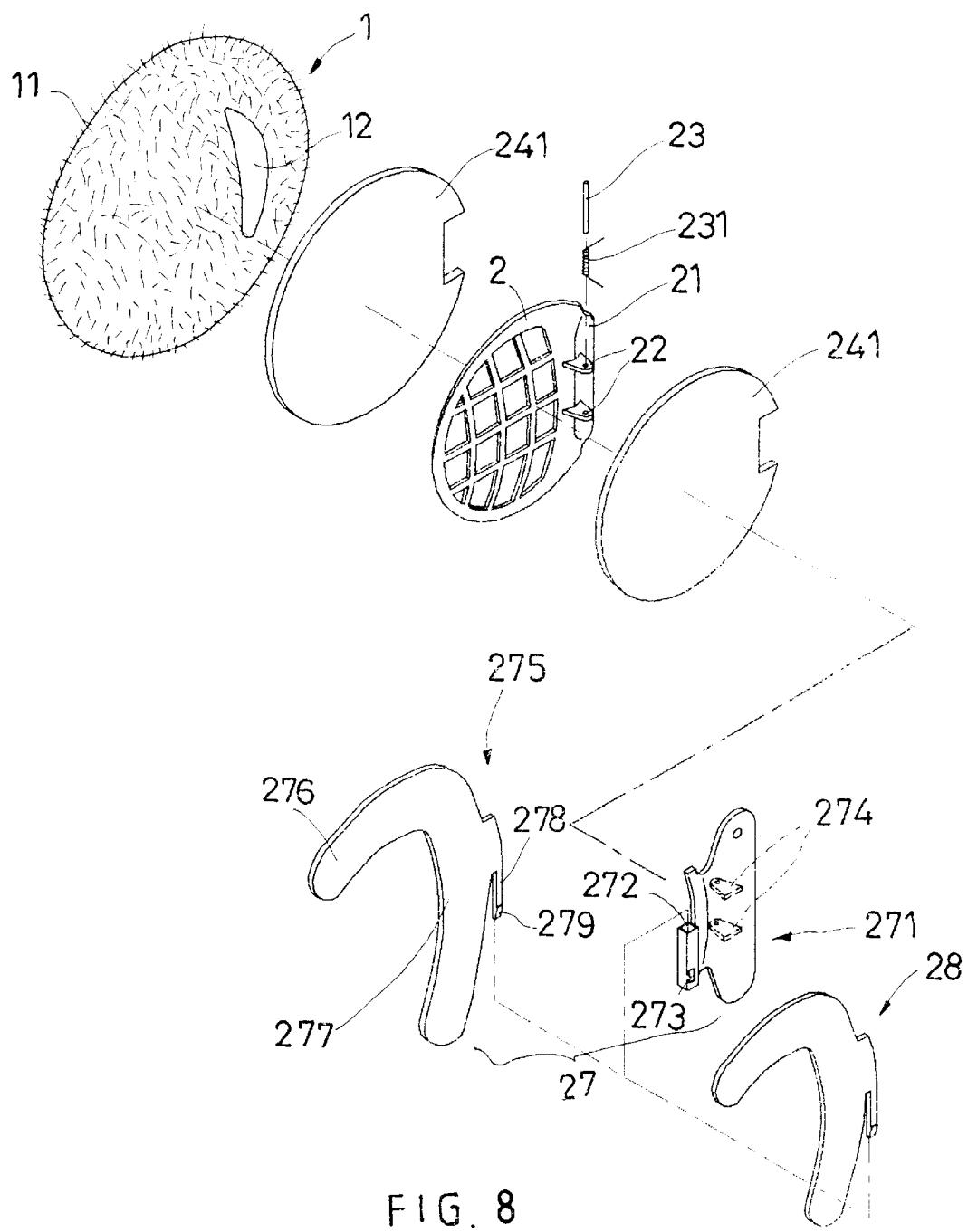
FIG. 8 is an exploded view of an alternate form of the present invention.
Figure 9:
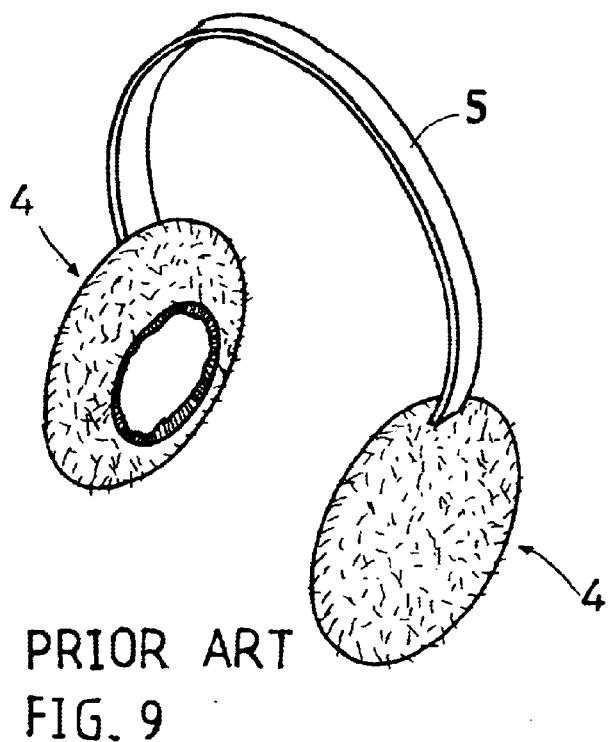
FIG. 9 is a perspective view of a headphone type earpiece assembly according to the prior art.
Figure 10:
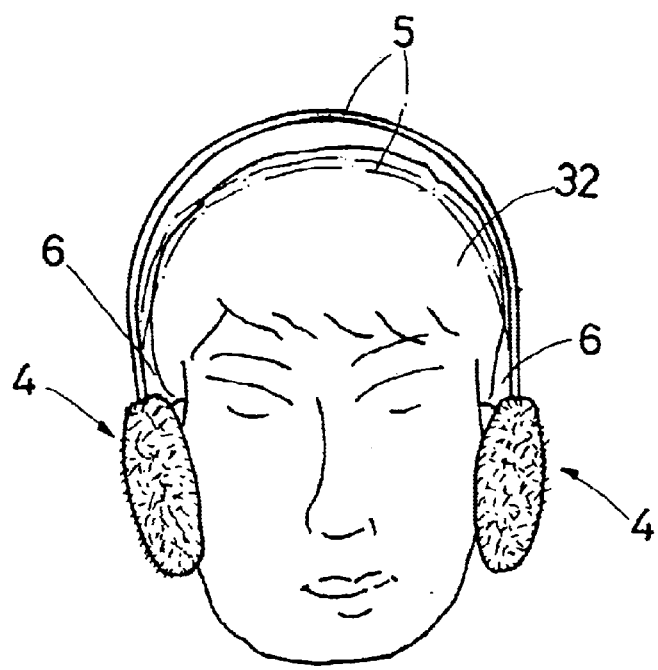
FIG. 10 shows the prior art headphone type earpiece assembly fastened to the user's head.

FIG. 8 shows an alternate form of the present invention. According to this embodiment, the clamping plate 27 or 28 comprises a rear mounting element 271 and a front clamping element 275. The rear mounting element 271 has two lugs 274 pivoted to the pivot pin 23 at the lugs 22 of the side flange 21 of the flat frame 2, a receptacle 272 at the front side, and a retaining hole 273 in the receptacle 272. The front clamping element 275 comprises a horizontal hook 276, a vertical clamping portion 277, a plug rod 278 downwardly suspended at the rear side, and a raised retaining portion 279 protruded from the free end of the plug rod 278. By plugging the plug rod 278 into the receptacle 272 to force the raised retaining portion 279 into the retaining hole 273, the clamping plate 275 is secured to the rear mounting element 271. This arrangement enables the user to attach a different size of clamping plate 275 to the rear mounting element 271 to form a different size of clamping plate 27 or 28.

A prototype of headphone type earpiece assembly has been constructed with the features of FIGS. 1–8. The headphone type earpiece assembly functions smoothly to provide all of the features discussed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. An earpiece comprising a soft cloth covering;

a flat frame mounted inside said soft cloth covering to support said soft cloth covering in shape, said frame having a side flange, two lugs protruded from said side flange, and a pivot pin connected between the lugs of said flat frame;

a clamping plate adapted to secure the respective earpiece to one of the user's ears, said clamping plate comprising a rear finger strip adapted to be connected to one end of a cord member, two lugs respectively protruded from said rear finger strip and pivoted to said pivot pin of said flat frame, a horizontal front hook adapted to hang the respective earpiece on the one of the user's ears, and a vertical front clamping portion adapted to clamp on the tragic lamina of the ear on which said horizontal front hook hangs; and a spring means mounted on said pivot pin and connected between said flat frame and said clamping plate to hold said clamping plate in a close position.

2. A headphone type earpiece assembly comprising two earpieces adapted to protect the user's ears and to keep the user's ears warm, and a cord member connected between said earpieces, wherein said earpieces each comprise:

a soft cloth covering;

a flat frame mounted inside said soft cloth covering to support said soft cloth covering in shape, said frame having a side flange, two lugs protruded from said side flange, and a pivot pin connected between the lugs of said flat frame;

a clamping plate adapted to secure the respective earpiece to one of the user's ears, said clamping plate comprising a rear finger strip connected to one end of said cord member, two lugs respectively protruded from said rear finger strip and pivoted to said pivot pin of said flat frame, a horizontal front hook adapted to hang the respective earpiece on the one of the user's ears, and a vertical front clamping portion adapted to clamp on the tragic lamina of the ear on which said horizontal front hook hangs; and a spring means mounted on said pivot pin and connected between said flat frame and said clamping plate to hold said clamping plate in a close position.

3. The headphone type earpiece assembly as claimed in claim 2, further comprising a soft pad provided between said flat frame and said clamping plate.

4. The headphone type earpiece assembly as claimed in claim 2, wherein said flat frame is slotted.

5. The headphone type earpiece assembly as claimed in claim 2 wherein the rear finger strip of the clamping plate of each of said earpieces has a wire hole for the mounting of said cord member.

6. The headphone type earpiece assembly as claimed in claim 2 wherein the clamping plate of each of said earpieces is comprised of a rear half forming said rear finger strip and the respective lugs, and a front half forming said horizontal front hook and said vertical front clamping portion and detachably connected to said rear half, said rear half having a receptacle and a retaining hole in said receptacle, said front half having a plug rod insertable in said receptacle and a retaining portion protruded from said plug rod for engaging said retaining hole in said receptacle.

* * * * *